(12) United States Patent
Ryan et al.

(10) Patent No.: US 6,302,159 B1
(45) Date of Patent: Oct. 16, 2001

(54) APPARATUS AND METHOD FOR CARRYING OUT FLOW THROUGH CHEMISTRY OF MULTIPLE MIXTURES

(75) Inventors: Paul Thomas Ryan; Kevin Auton, both of Huntingdon (GB)

(73) Assignee: Genomic Solutions, Inc., Ann Arbor, MI (US)

( * ) Notice: Subject to any disclaimer, the term of this patent is extended or adjusted under 35 U.S.C. 154(b) by 0 days.

(21) Appl. No.: 09/590,467

(22) Filed: Jun. 9, 2000

Related U.S. Application Data

(60) Provisional application No. 60/138,392, filed on Jun. 9, 1999.

(51) Int. Cl.[7] ............................... B65B 31/00; B67C 3/00
(52) U.S. Cl. ............................ 141/4; 141/44; 141/64; 141/100; 141/130; 141/285; 141/329
(58) Field of Search ........................... 141/4, 18, 37, 141/44, 51, 63, 64, 100, 129, 130, 285, 311 R, 329, 102; 73/864.01, 864.11; 422/63, 65, 100, 104

(56) References Cited

U.S. PATENT DOCUMENTS

| | | | |
|---|---|---|---|
| 4,810,471 | * | 3/1989 | Wachob et al. ..................... 422/103 |
| 4,951,512 | * | 8/1990 | Mazza et al. ....................... 73/861.23 |
| 4,962,041 | * | 10/1990 | Roginski ............................... 436/150 |
| 5,935,523 | * | 8/1999 | McCandless et al. ............... 422/100 |

* cited by examiner

*Primary Examiner*—Timothy L. Maust
(74) *Attorney, Agent, or Firm*—Rader, Fishman & Grauer PLLC

(57) ABSTRACT

An apparatus and method for chemical processing of multiple mixtures is disclosed. The apparatus provides selective purging of a liquid-phase of the mixtures. The apparatus can be used for processing many different types of mixtures under a wide variety of processing conditions, including but not limited to protein digestions, and is particularly well suited for processes requiring solid-liquid contacting. The apparatus includes an array of vessels or wells for containing the mixtures. The wells have openings that generally define a surface. A perforated plate and a film are disposed above the openings of the wells. The film is sandwiched between the perforated plate and the surface defined by the openings of the vessels, covering and sealing the vessels. A probe is used to perforate the film and to pressurize the vessels, which drives liquid out of the wells via through-holes formed in their bottoms.

16 Claims, 1 Drawing Sheet

APPARATUS AND METHOD FOR CARRYING OUT FLOW THROUGH CHEMISTRY OF MULTIPLE MIXTURES

CROSS REFERENCE TO RELATED APPLICATION

This application claims priority to U.S. Provisional Application Serial No. 60/138,392, filed Jun. 9, 1999.

BACKGROUND OF THE INVENTION

1. Field of the Invention

This invention relates to devices and techniques for chemical processing multiple mixtures, and more particularly, to an apparatus and method for sealing and purging multi-well reactors useful in high throughput protein analysis.

2. Discussion

Pharmaceutical and biomedical researchers continually seek new methods for rapidly identifying therapeutically important proteins. This interest has fueled an ongoing development of high throughput methods and instruments for carrying out protein analysis—an important element of an emerging scientific discipline known as proteomics. The field of proteomics generally involves systematic isolation, identification, and characterization of proteins present in biological samples. Proteomics typically employs two-dimensional gel electrophoresis (2DE) to separate complex mixtures of proteins. Once separated, individual proteins are subsequently identified and characterized based on their role in disease processes or performance in drug assays.

Steps in a typical proteomic protocol include: (1) solubilizing proteins using detergents to release proteins trapped in cells or tissue; (2) separating the proteins using two dimensional gel electrophoresis; (3) staining the gel to locate individual proteins; and (4) scanning the stained gel for proteins of interest. Scanning may include, for example, selecting proteins that occur in diseased tissue but are absent in healthy tissue. The protocol also includes: (5) picking or removing portions of the gel containing the proteins of interest; (6) breaking down the proteins removed from the gel into protein fragments (polypeptide residues); and (7) measuring the size (molecular weight) of the isolated proteins and residues using mass spectroscopy. Since proteins are heat labile, the mass spectroscopy technique usually employs a soft ionization technique, such as fast atom bombardment (FAB), field desorption (FD), atmospheric pressure ionization (API), or matrix-assisted laser desorption (MALDI). The last step in the protocol is (8) identifying protein fragments by comparing their sizes with other peptide (amino acid) sequences found in public and private databases. Once identified, researchers can evaluate the role of each protein in a disease process, and target the protein for drug intervention.

Currently, the steps in a proteomic analysis are done in a sequential and modular fashion. The output from one step is transferred manually to the next step, which makes the technique slow and cumbersome. It appears that recent advances in robotics, software design, and computer technology, could improve the sample throughput, rate of analysis, and reliability of the analysis. However, other problems remain.

The digestion step (6) is typically carried out in multi-well reactors, such as 96-well and 384-well microtiter plates. Microtiter plates comprise an array of depressions formed on a generally planar surface of a tray, and can be adapted to allow thermal processing of samples. Liquid samples, reagents, buffers, and the like, are normally added or removed from the wells by pipette, which may be automated using laboratory robotic systems. Solids may be placed in the wells, or may result from chemical reaction or changing conditions within a liquid sample (e.g., precipitation). In solid-liquid mixtures, one difficulty arises when using a pipette to purge the liquid-phase while retaining the solid-phase within the wells, as would occur, for example, when washing a solid sample with a liquid or when removing liquid-phase reactants and side products following chemical reaction. Although easy to add, liquids are hard to remove thoroughly from the wells because vacuum generated by the pipette is insufficient to overcome capillary forces that confine the liquid within the interstices of the solid or against the walls of the wells. The ability to thoroughly purge liquid from the wells is an important and common requirement of many processes, including protein digestions.

One way to ensure thorough removal of the liquid phase is to seal the wells and to apply sufficient pressure within the wells to purge liquid through holes provided in the bottom of each of the wells. The size of the holes is small enough to prevent passage of the solid phase during liquid purging; in the absence of an applied pressure, capillary forces are sufficient to retain the liquid phase in the wells. In this system, the desired product may be either the solid phase, which is retained in the wells, or the liquid phase, which is purged from the wells and can be collected in a second microtiter plate for example.

A robotic liquid handling system can be used to transfer reagents to the wells using a syringe pump coupled to a probe. The probe is comprised of inner and outer, coaxial cylindrical tubes. The inner tube, which extends outward from the end of the outer tube, aspirates or dispenses liquid; the outer tube dispenses gas. Before processing, each of the wells is sealed with a plastic cap having a tapered hole, which is sized to allow the probe to access the interior of the well. During the addition of liquid, the probe is inserted partway into the tapered hole so that air displaced by the liquid may escape from the well through the gap between the wall of the hole and the portion of the inner tube that extends beyond the end of the outer tube. When pressurizing the well, the probe is fully inserted in the tapered hole so that a substantially gas-tight seal is formed between the wall of the tapered hole and the exterior surface of the outer tube.

Although caps can work well, they have shortcomings. For example, large numbers of individual caps are difficult to handle and hard to seat properly in the wells. Although the caps can be manufactured by injection molding, the caps are relatively expensive unless groups of caps are molded in a single shot. But even when injecting molding large numbers of caps in a single shot, the tooling costs for multi-cavity molds can be high. Also, because the outer tube has to seal against the wall of the tapered hole, the caps wear out and must be replaced.

The present invention overcomes, or at least reduces, one or more of the problems set forth above.

SUMMARY OF THE INVENTION

The present invention provides an apparatus for processing mixtures, and is especially useful for processing solid-liquid mixtures that may require purging and/or replacement of the liquid phase. The apparatus includes a tray having wells that open along a surface. Each of the wells defines a vessel for receiving one of the mixtures. Individual vessels have a bottom portion and a through-hole located adjacent the bottom portion. For a particular vessel, the through-hole provides fluid communication between the vessel's interior and exterior. The size of the through-hole is small enough so that when little or no pressure gradient exists between the interior and exterior of the vessel, surface tension is sufficient to hold the liquid-phase in the vessel. However, when the vessel is pressurized, liquid flows out of the vessel via the through-hole. Regardless of the pressure gradient, the through-hole is sized to prevent any solids from exiting the vessel. This arrangement allows thorough purging of liquid from the vessels.

The film has first and second surfaces. The first surface of the film is disposed above (typically on) the surface of the tray, and covers and seals the wells (vessels). The apparatus also includes a plate having a first surface located adjacent the second surface of the film. The plate has an array of perforations that extend from the first surface of the plate to a second surface of the plate. Each of the perforations is substantially aligned with the wells following assembly of the apparatus. The film, which is typically a sheet of a low modulus plastic such as polyethylene, is a material that will flow without substantially tearing when pierced or perforated with a tool having a cross-sectional area about less than or equal to the cross-sectional area of the perforations in the plate. The cross-sectional area of the tool corresponds to a viewing plane having an outward normal approximately perpendicular to the second surface of the film when pierced. The apparatus may also include a probe for introducing fluid—gas or liquid—into the wells. Ordinarily the probe serves as the tool for piercing the film. One useful embodiment of the probe comprises coaxial inner and outer tubes. The inner and outer tubes are in selective fluid communication with a liquid source and a gas source, respectively, so that one may use a single probe to add liquid and gas to the vessels.

The present invention also provides a method of purging liquids from mixtures contained within an array of vessels. The method includes providing vessels that are adapted to receive the mixtures. Each of the vessels have an open top portion and a substantially closed bottom portion and a through-hole located adjacent the bottom portion. The through-hole provides fluid communication between the vessel and an environment exterior to the vessel. The method includes providing a unitary film for sealing the top portion of at least two of the vessels, and inserting a probe into one of the vessels to perforate the film and to provide a seal between the film and the probe exterior. The probe is in selective fluid communication with a gas source and channels gas into the vessel thereby forcing liquid out of the vessel via the through-hole. If the probe is in fluid communication with a liquid source, the method may also include channeling liquid into the vessel, while allowing displaced air to exit the vessel via a gap between the perforated film and the probe exterior.

DETAILED DESCRIPTION

Figure 1:
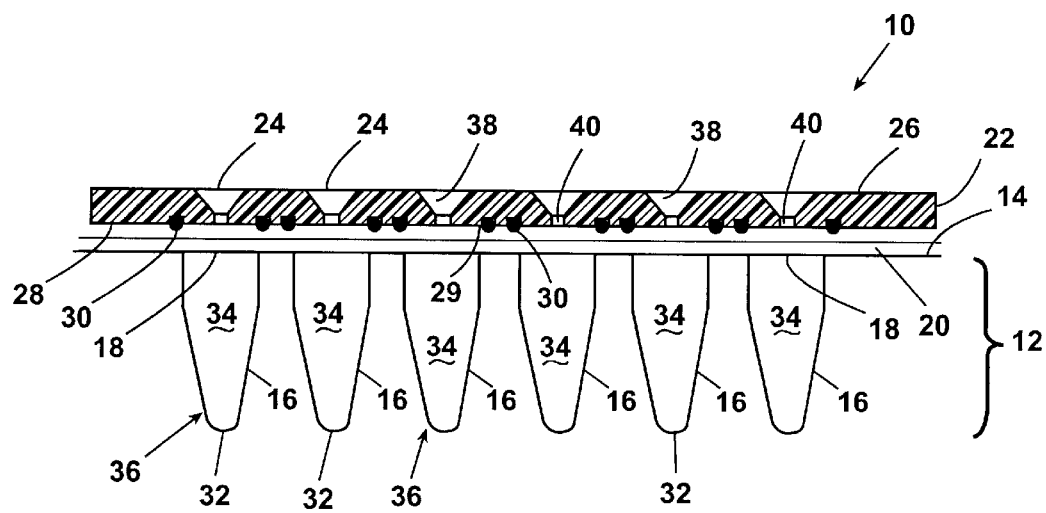
FIG. 1 shows a sketch of a cross-sectional side view of one embodiment of a multi-well (multi-vessel) reactor.

FIG. 1 shows a cross-sectional side view of one embodiment of a multi-well reactor 10, which allows selective purging of a liquid-phase. The reactor 10 can be used for processing many different types of mixtures under a wide variety of processing conditions, including but not limited to protein digestions, and is particularly well suited for processes requiring solid-liquid contacting. The reactor 10 shown in FIG. 1 includes a tray 12 having a generally planar top surface 14. Examples of a useful tray 12 include 96-well and 384-well microtiter plates. The tray 12 includes a plurality of wells 16 having openings 18 on the top surface 14 of the tray 12. The wells 16 serve as vessels for containing the mixtures. In an alternative embodiment, the reactor may comprise an array of individual vessels having openings that generally define a surface. In such an embodiment, the tray comprises the array of vessels and a rack for securing the vessels.

As shown in FIG. 1, a film 20 and perforated plate 22 are disposed above the top surface 14 of the tray 12. The film 20 is located between the perforated plate 22 and the top surface 14 of the tray 12. For clarity, FIG. 1 shows the film 20 displaced from the perforated plate 22 and the tray 12. When the reactor is assembled 10, however, the film 20 covers and seals the openings 18 of the wells 16. The film 20 may be secured to the tray 12 by clamping the perforated plate 22 to the tray 12, or by bonding the film 20 to the top surface 14 of the tray 12 using heat and pressure or an adhesive or both.

The perforated plate 22 has a plurality of tapered holes or perforations 24, which are in substantial alignment with the openings 18 of the wells 16, and extend from an upper surface 26 to a lower 28 surface of the perforated plate 22. Compliant o-rings 30, which are seated in circular grooves 29 formed in the lower 28 surface of the perforated plate 22, surround each of the perforations 24 and contact the film 20. The o-rings 30, which are usually fabricated from an elastomeric material, provide compliance between the tray 12 and the perforated plate 22. The o-rings 30 also account for irregularities on the surfaces 14, 28 of the tray 12 and the plate 22, and ensure proper sealing of the film 20 around individual wells 16. In other embodiments, the o-rings may be replaced with a compliant, perforated sheet (gasket) made of an elastomeric material. Each of the wells 16 has a through-hole 32 that extends from the interior 34 of the well 16 to the bottom 36 of the tray 12. The size of the through-holes 32 is small enough to prevent passage of the solids during liquid purging; and in the absence of an applied pressure, capillary forces are sufficient to retain the liquid phase in the wells 16.

In the embodiment shown in FIG. 1, the perforations 24 in the plate 22 are provided with a conical entry 38 and relatively narrow exit 40. The conical entry 38 helps guide a probe (not shown), which is used to introduce liquids and gas into the wells 16. The exit 40 region of the perforations 24 has a diameter slightly larger than the probe, and helps further align the probe.

Figure 2:
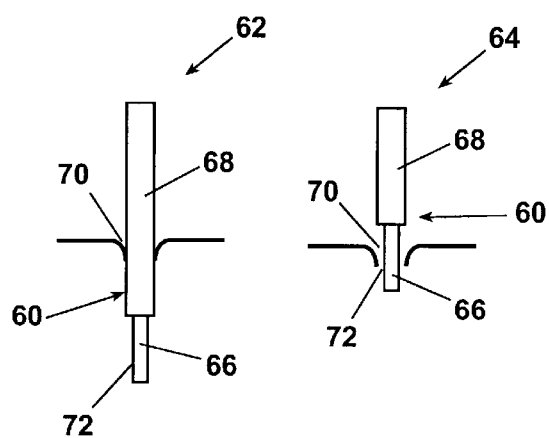
FIG. 2 shows positions of a probe during piercing of a film used to seal the multi-well reactor, during purging of a liquid-phase from the wells, and during the introduction of liquids into the wells.

FIG. 2 shows positions of a probe 60 during piercing of the film 20 and purging of the liquid-phase from the wells 16 (first probe position 62), and during the introduction of liquids into the wells 16 (second probe position 64). The probe 60 comprises inner 66 and outer 68 coaxial tubes and is connected to a liquid source and a gas source (not shown). Valves (not shown) provide selective fluid communication among the probe 60, the liquid source, and the gas source. The inner tube 66, which extends outward from the end of the outer tube 68, communicates with the liquid source via a syringe pump and aspirates or dispenses liquid into the interior 34 of the wells 16. The outer tube 68 communicates with a gas source, such as plant air or bottled nitrogen, and dispenses gas into the interior 34 of the wells 16 during liquid purging. To dispense a liquid, the film 20 must be pierced. As shown by the first probe position 62, the probe 60 is inserted through one of the perforations 24 of the plate 22—piercing the film 20—and continues until the outer tube 68 passes through the film 20. This probe 60 movement makes a hole 70 in the film 20 that is larger than the diameter of the inner tube 66. The probe 60 is then withdrawn. To introduce liquid into the wells 16, the probe 60 is inserted into one of the wells 16 to an extent where only the inner tube 66 protrudes through the film 20. This action is illustrated by the second probe position 64. Liquid entering the well 16 displaces air or other gases, which escape between the exterior surface 72 inner tube and the hole 70 in the film 12. It is important that air or other gases escape during the addition of liquids to the wells 16; otherwise pressure will rise in the interior 34 of the wells 16 causing an undesirable purging of liquid through the holes 32 in the bottom 36 of the wells 16.

Liquid can be purged from the wells 16 by inserting the probe 16 to the first probe position 62 so the outer tube 68 seals against the hole 70 in the film 20. The outer tube 68 dispenses gas into the well 16, which raises the pressure in the interior 34, and drives the liquid out of the well 16 via the through-hole 32. Since the exit 40 region of the perforations 24 in the plate 22 provide a close clearance fit with the outer tube 68 portion of the probe 60, multiple insertions of the probe 60 do not significantly enlarge the hole 70 in the film 20, despite any probe 60 misalignment prior to its insertion through the perforations 24.

The mechanical characteristics of the film 20 are critical to the operation of the reactor 10. When the film 20 is pierced it must flow rather than tear so that the hole 70 will seal about the surface of the outer tube 68. The film 20 must also be strong enough to withstand multiple insertions of the probe 60 while maintaining the integrity of the hole 70, which is necessary for adequate sealing. Experiments have shown that the softer (lower tensile modulus) plastics are preferable to harder (higher modulus) plastics. At room temperature, low-density polyethylene (LDPE) is an especially useful film 20 material. If the operating temperature is higher than the working temperature of LDPE, then a more crystalline (higher tensile modulus) film 20 can be used since it will soften somewhat at the elevated temperature. Examples of more crystalline materials include linear low-density polyethylene (LLDPE) and high-density linear polyethylene (HDLPE). Other useful film 20 materials, which are harder than LDPE, include cellulose acetate, cellulose acrylate-butyrate, polytetrafluoroethylene, polyamide, and polypropylene. In some cases, especially when using harder materials, it may be necessary to preheat the film 20 before piercing it to achieve a hole 70 that will seal satisfactorily.

Thicker films 20 tend to give more reliable sealing than thinner films 20, especially after multiple insertions. However, more force is required to pierce or perforate a thick film 20 than a thin film 20. In an alternative embodiment, a thicker film 20 can be used despite force limitations on the probe 60 or its support, by perforating the film 20 with a separate tool prior to using the film 20. The tool should be used to pierce the film 20 in the same manner as the probe 60. For example, the tool should have the same cross-sectional area as the probe 60. (The cross-sectional area corresponds to a viewing plane having a normal approximately perpendicular to the film 20 when pierced.) To ensure accurate alignment of the holes 70, the plate 22 can be overlaid on the film 20 during piercing with the tool to ensure accurate alignment of the holes 70, perforations 24, and wells 16 upon assembly of the reactor 10. In addition, there should be a close clearance fit between the exit 40 regions of the plate 20 perforations 24 and the tool.

Using a probe having an outside tube 68 diameter of 1.5 mm, LDPE film of thickness 50 microns to 250 microns has been found acceptable, with the optimum around 100 microns.

What is claimed is:

1. An apparatus for processing mixtures:

a tray having wells opening on a surface, each of the wells defining a vessel for receiving one of the mixtures, the vessel having a bottom portion and a through-hole located adjacent the bottom portion, the through-hole providing fluid communication between the vessel and an environment exterior to the vessel;

a film for sealing the wells, the film having first and second surfaces, the first surface of the film disposed above the surface of the tray and covering the wells; and a plate having a first surface located adjacent the second surface of the film, the plate having perforations extending from the first surface of the plate to a second surface of the plate, the perforations in substantial alignment with the wells;

wherein the film comprises a material that will flow without substantially tearing when pierced with a tool having a cross-sectional area about less than or equal to the cross-sectional area of the perforations in the plate.

2. The apparatus of claim 1, wherein the film is disposed on the surface of the tray.

3. The apparatus of claim 1, further comprising compliant o-rings surrounding each of the perforations in the plate, the o-rings located between the first surface of the plate and the second surface of the film.

4. The apparatus of claim 1, further comprising a compliant sheet sandwiched between the first surface of the plate and the second surface of the film, the compliant sheet having through-holes in substantial alignment with the perforations in the plate.

5. The apparatus of claim 1, wherein the perforations in the plate have a generally conical region adjacent the second surface of the plate and a generally cylindrical portion adjacent the first surface of the plate.

6. The apparatus of claim 1, wherein the film is a plastic.

7. The apparatus of claim 6, wherein the film is a polyethylene.

8. The apparatus of claim 7, wherein the film is a low-density polyethylene.

9. An apparatus for processing mixtures:

a tray having wells opening on a surface, each of the wells defining a vessel for receiving one of the mixtures, the vessel having a bottom portion and a through-hole located adjacent the bottom portion, the through-hole providing fluid communication between the vessel and an environment exterior to the vessel;

a film for sealing the wells, the film having first and second surfaces, the first surface of the film disposed above the surface of the tray and covering the wells;

a plate having a first surface located adjacent the second surface of the film, the plate having perforations extending from the first surface of the plate to a second surface of the plate, the perforations in substantial alignment with the wells; and a probe for introducing fluid in the wells, the probe having a cross-sectional area about less than or equal to the cross-sectional area of the perforations in the plate;

wherein the film comprises a material that will flow without substantially tearing when pierced with the probe.

10. The apparatus of claim 9, wherein the probe comprises inner and outer coaxial tubes.

11. The apparatus of claim 10, wherein the inner tube is in selective fluid communication with a liquid source.

12. The apparatus of claim 10, wherein the outer tube is in selective fluid communication with a gas source.

13. The apparatus of claim 10, wherein the inner tube extends outward from an end of the outer tube along a shared longitudinal axis.

14. A method of purging liquids from mixtures contained within an array of vessels, the method comprising:

providing vessels for receiving the mixtures, each of the vessels having an open top portion and a substantially closed bottom portion and a through-hole located adjacent the bottom portion, the through-hole providing fluid communication between the vessel and an environment exterior to the vessel;

providing a unitary film for sealing the top portion of at least two of the vessels;

inserting a probe into one of the vessels thereby perforating the film, the probe in selective fluid communication with a gas source; and allowing gas to flow into one of the vessels through the probe forcing liquid out of the vessel via the through-hole.

15. The method of claim 14, wherein the probe is in selective fluid communication with a liquid source.

16. The method of claim 15, further comprising allowing liquid to flow into one of the vessels through the probe.

* * * * *